(12) United States Patent
Ward et al.

(10) Patent No.: US 9,330,580 B2
(45) Date of Patent: May 3, 2016

(54) ASSAY WICK WITH ANALYTE FLUID SUFFICIENCY INDICATOR

(71) Applicant: Essentra Porous Technologies Corp., Colonial Heights, VA (US)

(72) Inventors: Bennett C. Ward, Midlothian, VA (US); Jian Xiang, Midlothian, VA (US); Stacey L. Tibbs, Colonial Heights, VA (US); Yelena N. Rogova, Richmond, VA (US)

(73) Assignee: Essentra Porous Technologies Corp., Colonial Heights, VA (US)

( * ) Notice: Subject to any disclaimer, the term of this patent is extended or adjusted under 35 U.S.C. 154(b) by 126 days.

(21) Appl. No.: 14/080,154

(22) Filed: Nov. 14, 2013

(65) Prior Publication Data
US 2014/0137792 A1    May 22, 2014

Related U.S. Application Data

(60) Provisional application No. 61/727,482, filed on Nov. 16, 2012.

(51) Int. Cl.
*G01N 21/75* (2006.01)
*G09F 3/02* (2006.01)
(Continued)

(52) U.S. Cl.
CPC . *G09F 3/02* (2013.01); *A24F 25/02* (2013.01); *B65D 81/24* (2013.01); *B65D 85/1081* (2013.01); *G09F 3/0294* (2013.01); *G09F 3/10* (2013.01); *G09F 2003/0272* (2013.01)

(58) Field of Classification Search
CPC ............ B01L 3/5023; G01N 2035/00128; G01N 35/1095; G01N 33/5008; G01N 33/558; G01N 1/2813; G01N 1/312; G01N 1/34; G01N 1/405; G01N 30/7233; G01N 33/0024; G01N 33/487; G01N 33/48771; G01N 33/5026; G01N 33/5029; G09F 3/02; G09F 3/0294; G09F 3/10; G09F 2003/0272; A24F 25/02; B65D 81/24; B65D 85/1081
See application file for complete search history.

(56) References Cited

U.S. PATENT DOCUMENTS

| | | |
|---|---|---|
| 5,310,525 A | 5/1994 | Churchouse et al. |
| 5,607,766 A | 3/1997 | Berger |

(Continued)

FOREIGN PATENT DOCUMENTS

EP        097959        1/1984

OTHER PUBLICATIONS

PCT International Search Report for International Application No. PCT/US13/70094, Jan. 30, 2014, 2 pages.

*Primary Examiner* — Dennis M White
(74) *Attorney, Agent, or Firm* — Don J. Pelto, Esq.; Sheppard, Mullin, Richter & Hampton LLP

(57) ABSTRACT

A wick for use in determining sufficiency of an amount of analyte fluid provided to an analyte test section of an assay device is provided. The wick comprises a primary wick portion attached or attachable to the analyte test section so as to be in fluid communication therewith. The primary wick portion has a receiving surface adapted for receiving the analyte fluid and is configured to draw the analyte fluid from a first area to a second area of the primary wick portion. The assay wick further comprises an indicator portion having a contrasting visual characteristic. The indicator surface is covered by at least a portion of the primary wick portion, which comprises a wicking material that becomes more light transmissive when wetted by the analyte fluid. The contrasting visual characteristic is viewable through the at least a portion of the primary wick portion only when the at least a portion of the primary wick portion is suffused by the analyte fluid.

21 Claims, 6 Drawing Sheets

(51) Int. Cl.
  *G09F 3/00* (2006.01)
  *G09F 3/10* (2006.01)
  *A24F 25/02* (2006.01)
  *B65D 81/24* (2006.01)
  *B65D 85/10* (2006.01)

(56) References Cited

U.S. PATENT DOCUMENTS

| | | |
|---|---|---|
| 5,620,641 A | 4/1997 | Berger |
| 5,629,186 A | 5/1997 | Yasukawa et al. |
| 5,633,082 A | 5/1997 | Berger |
| 6,103,181 A | 8/2000 | Berger |
| 6,156,272 A | 12/2000 | Lee et al. |
| 6,330,883 B1 | 12/2001 | Berger |
| 6,840,692 B2 | 1/2005 | Ward et al. |
| 7,290,668 B2 | 11/2007 | Ward et al. |
| 2004/0253142 A1 | 12/2004 | Brewster et al. |
| 2006/0029924 A1* | 2/2006 | Brewster et al. ............ 435/4 |
| 2008/0251599 A1 | 10/2008 | Ward et al. |
| 2010/0024526 A1 | 2/2010 | Colvin, Jr. et al. |
| 2012/0071789 A1 | 3/2012 | Jowett et al. |

* cited by examiner

ASSAY WICK WITH ANALYTE FLUID SUFFICIENCY INDICATOR

CROSS REFERENCE TO RELATED APPLICATION

This application claims priority to U.S. Provisional Application 61/727,482 filed Nov. 16, 2012, the complete disclosure of which is incorporated herein by reference in its entirety.

BACKGROUND OF THE INVENTION

The invention relates generally to hygroscopic wicks and, more particularly, to fiber wicks configured for transporting analyte fluids in assay devices.

Various assay devices are known for use in the home, office, clinic, hospital or doctor's surgery for providing an analytical result which is rapid and which requires a minimal degree of skill and involvement by the user. Examples include test devices or assays for pregnancy and fertile period (ovulation) determination.

Typical assay devices comprise a housing, a reaction medium positioned in the housing, upon which the assay chemistry occurs, and a wick for collecting the liquid to be assayed and transferring it to the reaction medium. In general, the assay device should merely require that a collection portion of the device be contacted with a sample (e.g., a urine sample for pregnancy testing), and thereafter no further user actions are required. The sample is carried from the collection portion to the reaction medium by the wick. Observation of changes to the reaction medium or a substrate carrying the reaction medium provide an analytical result. Ideally, the analytical result should be observable within a matter of minutes following sampling.

The actual analytic techniques used to obtain the results typically determine the presence or absence of, and/or quantify the amount of various analytes in, tissues and fluids of organisms. Currently most diagnostic testing is done with blood, urine, fecal material, saliva, or tissue biopsy. Assay devices for collecting and reacting these materials can be used for, inter alia, pregnancy and ovulation tests, drug-of-abuse tests, and infectious disease tests.

One problem with standard assay devices, particularly those designed for self-testing in the home, is that the user may have difficulty determining whether enough of the analyte fluid or other material has been provided to the sample collector. This may be a particular problem with urine sampling devices because urine may be relatively colorless. One approach to solving this problem is to provide diagnostic assay devices with a color change indicator to signal that sufficient analyte-containing liquid (e.g., urine, saliva, plasma) has been collected by the sample collector. In wick-based devices, the color change generally indicates that the wicking component has been "wetted out" with the analyte fluid.

In such devices, however, the color change indication is based on the presence of a dye or colored substance that undergoes a change when wetted with water or other aqueous liquid. U.S. patent application Ser. No. 10/495,714 ('714 Application"), for example, describes sample collectors having wicking components (termed "bibulous members") that contain a dye that changes color as the result of a pH change. In some disclosed examples, a dry wick contains the acid form of a pH-sensitive dye which, upon wetting by the analyte-containing solution, experiences a pH change to more basic conditions, resulting in a color change. The color change is said to be distinctly visible to the eye so as to indicate sufficient analyte solution is present to both conduct the diagnostic analysis and effect color change.

Other compounds can undergo a color change when wetted. For example, a commonly used indicator is cobalt chloride ($CoCl_2$). Anhydrous cobalt chloride is blue. When it bonds with two water molecules, ($CoCl_2.2H_2O$), it turns purple. Further hydration results in the pink hexaaquacobalt (II) chloride complex $[Co(H_2O)_6]Cl_2$.

These visual indications are the result of employing pH-sensitive dye molecules, such as phloxine B or bromophenol blue, along with pH altering reagents (acids or bases), or inorganic compounds. In either case, use of these chemical compounds may interfere with, or otherwise alter, the analyte itself or the diagnostic assay. This may reduce the sensitivity of the assay or lead to false negative or false positive results.

Another approach to sufficiency indication is to permanently color the wicking material or provide it with a permanently colored marker and cover the wick or marker with an additional material that is substantially opaque when dry and light transmittent when wet. The above-mentioned '714 Application discloses the use of such materials as sugar paste, nitrocellulose membranes, and nylon microporous membranes to cover an acetate strip affixed to the wicking material. This approach, however, may introduce additional uncertainty due to the separation of the cover material from the wicking material. It also introduces significant complexity and cost to the production of the wick.

SUMMARY OF THE INVENTION

The present invention provides a wick for use in determining sufficiency of an amount of analyte fluid provided to an analyte test section of an assay device. The wick comprises a primary wick portion attached or attachable to the analyte test section so as to be in fluid communication therewith. The primary wick portion has a receiving surface adapted for receiving the analyte fluid into a first area of the primary wick portion and is configured to draw the analyte fluid from the first area to a second area of the primary wick portion. The wick further comprises an indicator portion having a contrasting visual characteristic. The indicator portion is disposed so that some or all of the indicator portion is covered by at least a portion of the primary wick portion. The at least a portion of the primary wick portion comprises a first wicking material that becomes more light transmissive when the first wicking material is wetted by the analyte fluid. The contrasting visual characteristic is viewable through the at least a portion of the primary wick portion only when the at least a portion of the primary wick portion is suffused by a predetermined amount of the analyte fluid.

BRIEF DESCRIPTION OF THE DRAWING

The invention can be more fully understood by reading the following detailed description together with the accompanying drawing, in which like reference indicators are used to designate like elements, and in which.

DETAILED DESCRIPTION OF THE INVENTION

Figure 1:
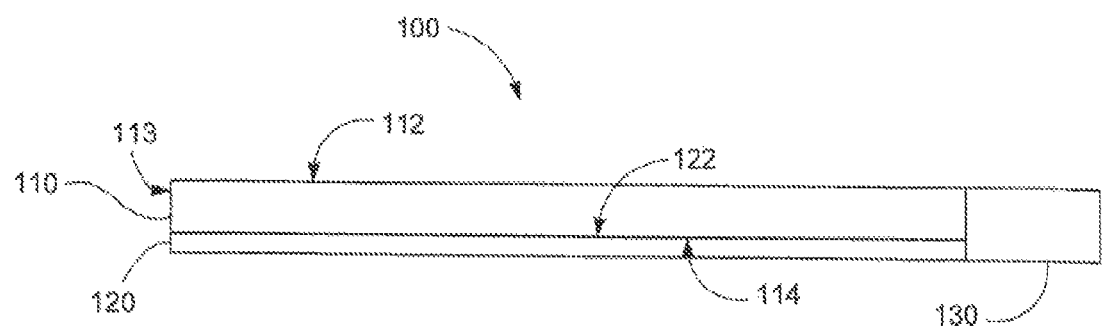
FIG. 1 is a side view of an assay wick according to an embodiment of the invention.

The present invention provides a visual sufficiency indicator system that does not contain color changing additives or reagents that change as the result of a chemical change or reaction. Embodiments of the present invention provide assay devices having wicks in which the wicking material itself is configured so that it reveals a colored or indicia-emblazoned indicator when it has absorbed a desired amount of analyte fluid. This is accomplished through the use of selected materials that tend to become more light transmittent when wetted with the particular analyte fluid and the tailoring of other physical characteristics of the wick so that the wick becomes sufficiently translucent to allow an underlying indicator layer to be viewed.

The tendency for certain materials such as cotton cloth and paper to become more translucent when wetted is well-known. These materials are formed from a multiplicity of cotton or cellulose fibers. While such fibers are essentially transparent or translucent, their refraction index is significantly different from that of air. When light is presented to a sheet formed from a multiplicity of these fibers, the disparity in refraction index cause a high degree of scattering and reflection back toward the source. The result is an appearance of an opaque or slightly translucent white material. When wetted with water, however, these same material become more light transmittent. This is because their refractive indexes are similar to that of water. With less disparity in refractive index, less scattering occurs and more light passes through the material where it can be reflected back by an underlying surface.

In an illustrious embodiment of the invention, an assay wick has two primary components; (1) a primary wick material that provides most or all of the wicking potential and (2) an indicator material or layer positioned underneath or embedded within the primary wick material. The primary wick material is formed from fibers that are selected so that (a) the primary wick material adequately wicks a predetermined analyte fluid and (b) visually obscures the indicator material when dry and visually reveals the indicator material when wetted by a predetermined amount of the predetermined analyte fluid type. The indicator material is configured with a contrasting color or graphical indicium that is viewable through the primary wick material when the wick material is suffused with a sufficient amount of the analyte fluid.

As used herein the term analyte fluid means a fluid sample that is to be analyzed for the presence of one or more analytes in the fluid sample and/or to quantify the amount of one or more analytes present in the fluid sample. The wicking materials used in the various embodiments of the present invention need to provide rapid, controlled transport of analyte fluids. This can sometimes be accomplished by using fiber or other materials that have a natural affinity for the analyte fluid of interest. In many instances, however, the materials of the wick must be treated to enhance their affinity (or eliminate their phobicity) for the analyte fluid.

For the present application, however, wicking capability is not the only consideration. The material must also exhibit the above-described effect in which translucency increases upon wetting with the analyte fluid. This not only limits the base material that can be used, it also restricts or eliminates the use of certain additives that would limit the inherent translucency of the material.

With the above considerations in mind, various embodiments of the invention will be described. With reference to FIG. 1, an assay wick 100 according to an embodiment of the invention includes a primary wick layer 110 and an indicator layer 120. The primary wick layer 110 has an upper or receiving surface 112, some or all of which may be presented for receiving an analyte fluid, and a lower surface 114. In some embodiments, the primary wick layer 110 may in addition or instead receive analyte fluid through an end surface 113 from an external source or from another wick element. The primary wick layer 110 is configured for receiving the analyte fluid through the upper surface 112 and/or the end surface 113 and for transporting the analyte fluid from one portion of the primary wick layer 110 to another portion of the primary wick layer 110 that includes or is in fluid communication with an analyte test section 130. The indicator layer 120 is adhered or otherwise attached to the bottom surface 114 of the primary wick layer 110. As will be discussed in more detail, the primary wick layer 110 is formed from a material that exhibits increased light transmittance when wetted by a particular analyte fluid.

The indicator layer 120 may be formed from a material having a contrasting visual characteristic (i.e., a distinct color or other appearance variation such as a pattern or indicium) relative to the visual appearance of the primary wick layer 110 and/or the analyte fluid. Alternatively or in addition, the indicator layer 120 may include or have applied to at least a portion of its upper surface an indicia layer 122. Some or all of the indicia layer 122 may be formed with a contrasting color selected to distinguish the indicia layer 122 from the primary wick layer 110 and the analyte fluid when the primary wick layer 110 is wetted with the analyte fluid. Further, some or all of the indicia layer 122 may be provided with a graphical indicium formed using a color contrasting from the primary wick layer 110 and the analyte fluid when the primary wick layer 110 is wetted with the analyte fluid. The graphical indicium may be any suitable graphic such as a logo, text, pattern, symbol or sign. In some embodiments, the indicium may include one or more instructions relating to the use of the wick and/or the assay device in which the wick is incorporated. The indicator portion 120 may be a monolithic body or may be a layered or composite structure in which the uppermost layer has or carries the distinguishing color or indicia. Alternatively or in addition, the indicator portion 120 may be formed from materials that, like the material of the primary wick portion 110, exhibit increased light transmittance when wetted with the analyte fluid. In such embodiments, the indicator portion 120 may be loaded with a colored particulate or other material that provides the contrasting visual characteristic when the indicator portion 120 is wetted.

Figure 2:
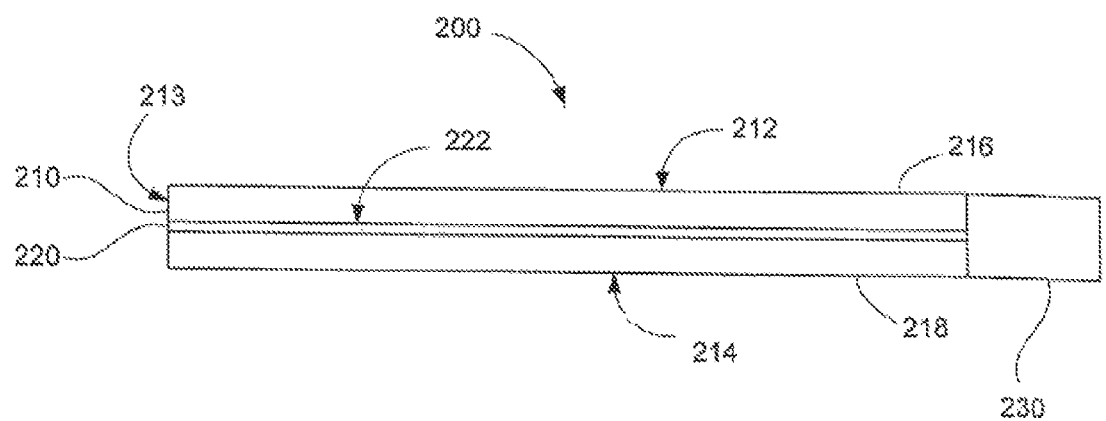
FIG. 2 is a side view of an assay wick according to an embodiment of the invention.

With reference to FIG. 2, an assay wick 200 according to an embodiment of the invention includes a primary wick portion 210 having an upper wick layer 216 and a lower wick layer 218. An indicator layer 220 is disposed intermediate the upper and lower wick layers 216, 218. The upper wick layer 216 has an upper or receiving surface 212, some or all of which may be presented for receiving an analyte fluid, and a lower surface 214. In some embodiments, the primary wick layer 210 may in addition or instead receive analyte fluid through an end surface 213 from an external source or from another wick element. The upper wick layer 216 is configured for receiving the analyte fluid through the upper surface 212 and/or the end surface 213 and for transporting the analyte fluid to another portion of the primary wick layer 210 that includes or is in fluid communication with an analyte test section 230. The indicator layer 220 is adhered or otherwise attached to the bottom surface 214 of the primary wick layer 210. The lower wick layer 218 may be adhered to the indicator layer 220 or, in some embodiments, may be adhered or otherwise attached to the upper wick layer 216 through or around the indicator layer 220. Alternatively, one or both of the indicator layer 220 and the lower wick layer 218 may be held in contact with the upper wick layer 216 and with one another by mechanical means such as fasteners or a casing.

As in the previous embodiment, the indicator layer 220 may be formed from a material having a contrasting visual characteristic relative to the visual appearance of the upper wick layer 216 and/or the analyte fluid. Alternatively or in addition, the indicator layer 220 may include or have applied to at least a portion of its upper surface an indicia layer 222. Some or all of the indicia layer 222 may be formed with a contrasting color selected to distinguish the indicia layer 222 from the upper wick layer 216 and the analyte fluid when the upper wick layer 216 is wetted with the analyte fluid. Further, some or all of the indicia layer 222 may be provided with a graphical indicium formed using a color contrasting from the upper wick layer 216 and the analyte fluid when the upper wick layer 216 is wetted with the analyte fluid. The indicator portion 220 may be a monolithic body or may be a layered or composite structure in which the uppermost layer has or carries the distinguishing color or indicia. Alternatively or in addition, the indicator portion 220 may be formed from materials that, like the material of the primary wick portion 210, exhibit increased light transmittance when wetted with the analyte fluid. In such embodiments, the indicator portion 220 may be loaded with a colored particulate or other material that provides the contrasting visual characteristic when the indicator portion 220 is wetted.

Figure 3:
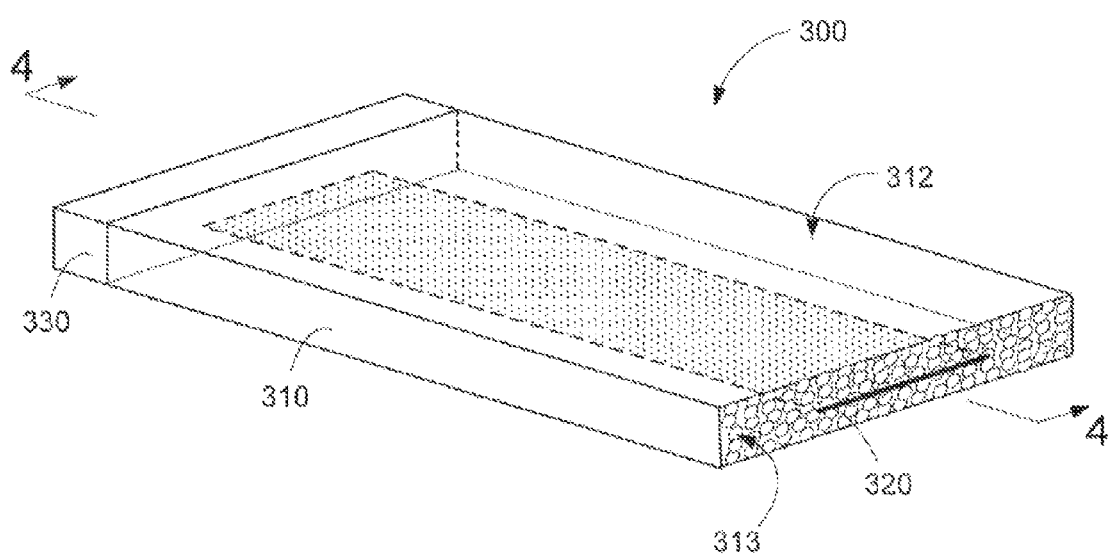
FIG. 3 is a perspective view of an assay wick according to an embodiment of the invention.
Figure 4:
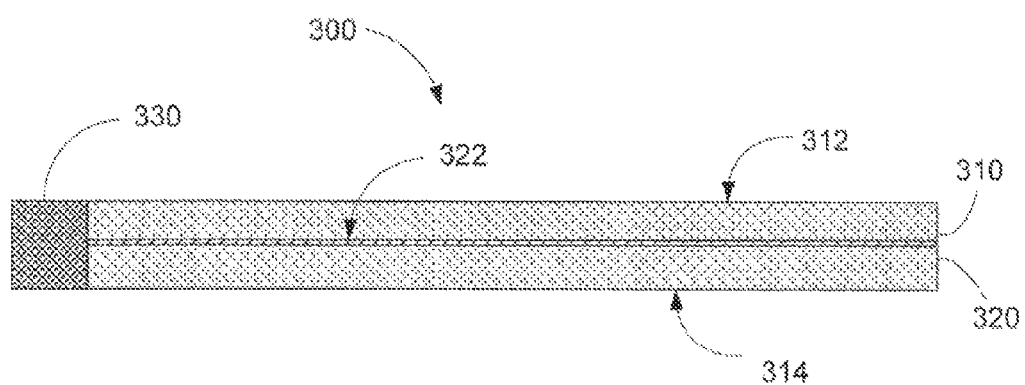
FIG. 4 is a section view of the assay wick of FIG. 3.

With reference to FIGS. 3 and 4, an assay wick 300 according to an embodiment of the invention includes a primary wick layer 310 and an indicator layer 320. The primary wick layer 310 has an upper or receiving surface 312, some or all of which may be presented for receiving an analyte fluid, and a lower surface 314. In some embodiments, the primary wick layer 310 may in addition or instead receive analyte fluid through an end surface 313 from an external source or from another wick element. The primary wick layer 310 is configured for receiving the analyte fluid through the upper surface 312 and/or the end surface 313 and for transporting the analyte fluid from one portion of the primary wick layer 310 to another portion of the primary wick layer 310 that includes or is in fluid communication with an analyte test section 330.

The indicator layer 320 is embedded or encased entirely within the primary wick layer 310. The indicator layer 320 may be formed from a material having a contrasting visual characteristic relative to the visual appearance of the primary wick layer 310 and/or the analyte fluid. Alternatively or in addition, the indicator layer 320 may include or have applied to at least a portion of its upper surface an indicia layer 322. Some or all of the indicia layer 322 may be formed with a contrasting color selected to distinguish the indicia layer 322 from the primary wick layer 310 and the analyte fluid when the primary wick layer 310 is wetted with the analyte fluid. Further, some or all of the indicia layer 322 may be provided with a graphical indicium formed using a color contrasting from the primary wick layer 310 and the analyte fluid when the primary wick layer 310 is wetted with the analyte fluid. The indicator portion 320 may be a monolithic body or may be a layered or composite structure in which the uppermost layer has or carries the distinguishing color or indicia. Alternatively or in addition, the indicator portion 320 may be formed from materials that, like the material of the primary wick portion 310, exhibit increased light transmittance when wetted with the analyte fluid. In such embodiments, the indicator portion 320 may be loaded with a colored particulate or other material that provides the contrasting visual characteristic when the indicator portion 320 is wetted.

Figure 5:
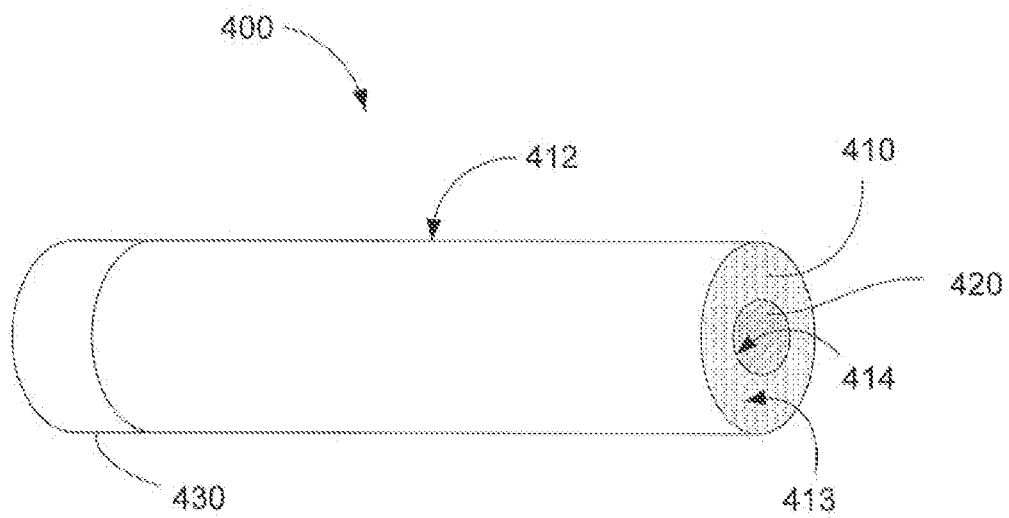
FIG. 5 is a perspective view of an assay wick according to an embodiment of the invention.
Figure 6:
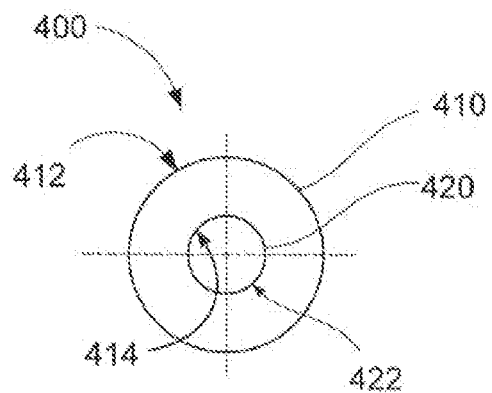
FIG. 6 is an end view of the assay wick of FIG. 5.

With reference to FIGS. 5 and 6, an assay wick 400 according to an embodiment of the invention includes a cylindrical primary wick portion 410 surrounding an indicator portion 420. The primary wick portion 410 has an outer or receiving surface 412, some or all of which may be presented for receiving an analyte fluid, and an inner surface 414. In some embodiments, the primary wick portion 410 may in addition or instead receive analyte fluid through an end surface 413 from an external source or from another wick element. The primary wick portion 410 is configured for receiving the analyte fluid through the outer surface 412 and/or the end surface 413 and for transporting the analyte fluid from one portion of the primary wick portion 410 to another portion of the primary wick portion 410 that includes or is in fluid communication with an analyte test section 430.

The indicator portion 420 may be formed as a circular cylinder, but may also be a prism or other shape. The outer surface 422 of the indicator portion 420 is in contact with the inner surface 414 of the primary wick portion 410. The indicator portion 420 may be formed from a material having a contrasting visual characteristic relative to the visual appearance of the primary wick portion 410 and/or the analyte fluid. Alternatively or in addition, the indicator portion 420 may include or have applied to at least a portion of its outer surface an indicia portion 422. Some or all of the indicia portion 422 may be formed with a contrasting color selected to distinguish the indicia portion 422 from the primary wick portion 410 and the analyte fluid when the primary wick portion 410 is wetted with the analyte fluid. Further, some or all of the indicia portion 422 may be provided with a graphical indicium formed using a color contrasting from the primary wick portion 410 and the analyte fluid when the primary wick portion 410 is wetted with the analyte fluid. The indicator portion 420 may be a monolithic body or may be a layered or composite structure in which the radially outermost layer has or carries the distinguishing color or indicia. Alternatively or in addition, the indicator portion 420 may be formed from materials that, like the material of the primary wick portion 410, exhibit increased light transmittance when wetted with the analyte fluid. In such embodiments, the indicator portion 420 may be loaded with a colored particulate or other material that provides the contrasting visual characteristic when the indicator portion 420 is wetted.

Figure 7:
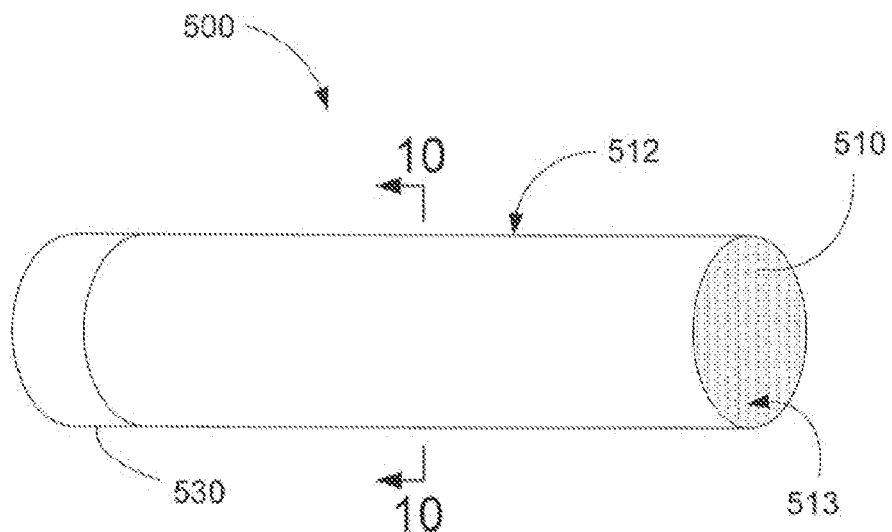
FIG. 7 is a perspective view of an assay wick according to an embodiment of the invention.
Figure 8:
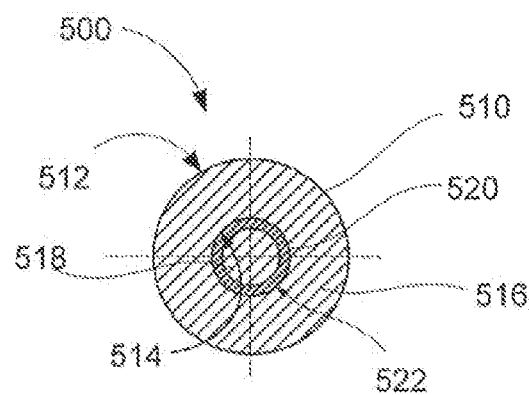
FIG. 8 is a section view of the assay wick of FIG. 7.

With reference to FIGS. 7 and 8, an assay wick 500 according to an embodiment of the invention includes a cylindrical primary wick portion 510 having an outer wick portion 516 surrounding an indicator portion 520. The indicator portion 520 may be an annular cylinder or tube or may be a thin band or strip. In either case, the indicator portion surrounds an inner wick portion 518. The primary wick portion 510 has an outer or receiving surface 512, some or all of which may be presented for receiving an analyte fluid, and an inner surface 514. In some embodiments, the primary wick portion 510 may in addition or instead receive analyte fluid through an end surface 513 from an external source or from another wick element. The primary wick portion 510 is configured for receiving the analyte fluid through the outer surface 512 and/or the end surface 513 and for transporting the analyte fluid from one portion of the primary wick portion 510 to another portion of the primary wick portion 510 that includes or is in fluid communication with an analyte test section 530.

The indicator portion 520 has an outer surface 522 that is in contact with the inner surface 514 of the primary wick portion 510. The indicator portion 520 may be formed from a material having a distinct color or other appearance variation relative to that of the primary wick portion 510 and/or the analyte fluid. Alternatively or in addition, the indicator portion 520 may include or have applied to at least a portion of its outer surface an indicia portion 522. Some or all of the indicia portion 522 may be formed with a contrasting color selected to distinguish the indicia portion 522 from the primary wick portion 510 and the analyte fluid when the primary wick portion 510 is wetted with the analyte fluid. Further, some or all of the indicia portion 522 may be provided with a graphical indicium formed using a color contrasting from the primary wick portion 510 and the analyte fluid when the primary wick portion 510 is wetted with the analyte fluid.

Figure 9:
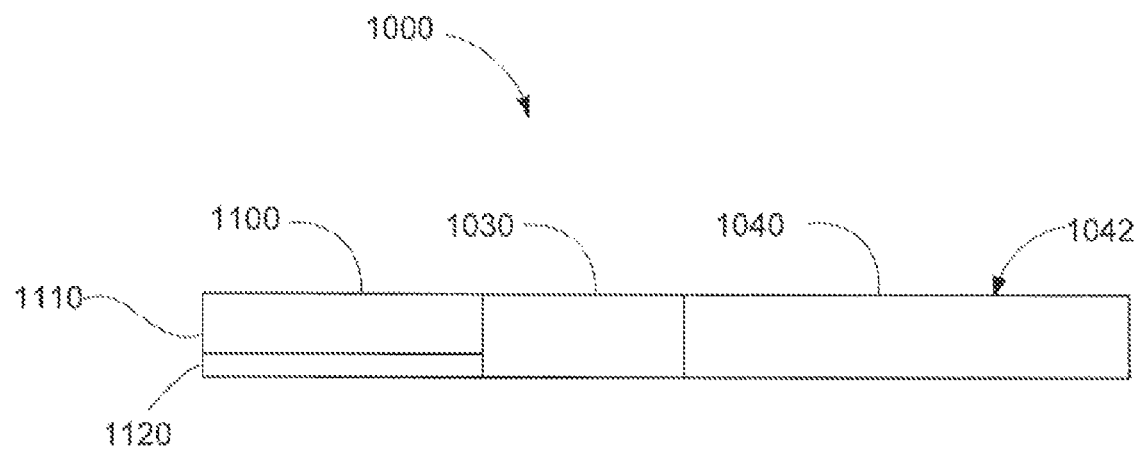
FIG. 9 is a side view of an assay wick according to an embodiment of the invention.

In the preceding embodiments, the combination of the primary wick material and the indicator material act as an analyte fluid sufficiency indicator. In each of these embodiments, the sufficiency indicator is positioned in an area upstream of an analyte test section. It will be understood, however, that any of these sufficiency indicators could, alternatively or in addition, be placed downstream of an analyte test section. In the general schematic illustration of FIG. 9, an assay wick 1000 has a fluid receiving portion 1040 configured for receiving an analyte fluid through a receiving surface 1042 and transporting the analyte fluid to an analyte test section 1030. The analyte test section 1030 may have reagents disposed therein that react with the analyte fluid and provide a visual indication of a reaction result. The analyte test section 1030 is also configured to transport at least a portion of the analyte fluid to a sufficiency indicator 1100. In the schematic illustration of FIG. 9, the sufficiency indicator 1100 has a primary wick layer 1110 and an indicator layer 1120 that are similar in configuration and operation to the primary wick layer 110 and indicator layer 120 of wick 100 in FIG. 1. It will be understood, however, that the wick/indicator combinations of any of the preceding embodiments could be used.

The advantage of placing a sufficiency indicator downstream of the analyte test section is that it can be used to assure that a sufficient amount of analyte fluid reached the analyte test section.

Each of the fluid receiving portion 1040, analyte test section 1030, and at least the wick portion of the indicator 1100 may be or include a wicking material. The wicking material of any of these three sections of the wick 1000 may be the same or different from the other sections. In some embodiments, all three of the fluid receiving portion 1040, the analyte test section 1030, and the wick portion of the sufficiency indicator 1100 comprise the same wicking material. In a particular embodiment, all three are formed as a single integral wick element.

The wicking materials used in the various embodiments of the invention may be or include any material that can sufficiently adsorb and wick an analyte fluid of interest. The wicking material in sufficiency indicator portions must also exhibit enhanced translucency when wetted by the analyte fluid of interest. As has already been discussed, materials formed from certain natural fibers such as cellulose and cotton exhibit the required enhanced translucency when wetted with water-based analyte fluids. Such materials can also be used to form wicks according to the invention. It has been found, however, that materials formed from synthetic polymers may be preferable in many applications.

Fiber-based materials used in wicks of the invention may be woven or non-woven materials. In certain embodiments, the wicks of the invention may be bonded fiber structures comprising interconnection networks of highly dispersed continuous and/or staple fibers bonded to each other at spaced apart points of contact. As described in U.S. Pat. Nos. 5,607,766, 5,620,641, 5,633,082, 6,103,181, 6,330,883, and 6,840,692, the complete disclosure of each of which is incorporated herein by reference in its entirety, such bonded fiber structures may be formed using a wide variety of fiber types and manufacturing methods. Of particular utility are structures made from fiber webs that are formed into substantially self-sustaining, three-dimensional porous components. The dispersed bonded fibers of these structures define tortuous passages through the structure that can provide very high surface areas and porosity, and may be formed in a variety of sizes and shapes.

Many polymer materials that can be used to form the fibers used to make bonded fiber structures including but not limited to polyolefins, polyesters, polyurethanes, and polyamides, and copolymers thereof. Particular materials include polyethylene, low density polyethylene, polypropylene, polyethylene terephthalate, polybutylene terephthalate and nylon.

It will be understood, however, that not all of the above polymer materials will be suited for sufficiency indicators to be used with a particular analyte fluid. Some may not have a refraction index sufficiently close to that of the analyte fluid. Others may simply not be usable to wick the analyte fluid without the use of additives that could affect translucency. For example, hydrophobic materials (e.g., polypropylene) may not be usable in an assay wick for a urine test without a surfactant.

The ideal fiber for use in sufficiency indicators of the invention is one that is formed, at least in part, from a polymer material that naturally has a refraction index close to that of the analyte fluid of interest and that can be used to form a bonded fiber structure having the desired fluid transport characteristics. Monocomponent fibers, bicomponent (or other multicomponent) fibers or combinations of both may be used. In bicomponent fibers, at least one of the two fiber components (and preferably both) would have a refractive index close to that of the analyte fluid. In particular embodiments, wick materials may be formed from sheath/core bicomponent fibers in which at least the sheath component and preferably both the sheath and the core components are formed from polymer materials exhibiting a refractive index close to that of the analyte fluid.

Many assay wick test kits are configured for collection and testing of urine or saliva. Such wicks are described in detail in U.S. Pat. No. 7,290,668, the complete disclosure of which is incorporated herein by reference in its entirety. It is highly desirable, particularly in home test kits, to provide the user of these kits an immediate indication that a sufficient amount of urine or saliva has been provided. Accordingly, a sufficiency indicator according to the invention must incorporate a wick material that has an affinity for water and that exhibits increased translucency when wetted with water.

It has been found that structures formed from polyolefin fibers, generally, and fibers comprising polyethylene (PE) and polypropylene (PP), in particular, exhibit suitable enhanced translucency in water. Fibers formed from other polymers such as polyethylene terephthalate (PET), polybutylene terephthalate (PBT), and polyamides may also be usable.

Bonded fiber structures having both the desired wicking capability and translucency behavior can be formed from PE monocomponent fibers. A particularly suitable bonded fiber structure, however, may be formed from sheath/core bicomponent fibers having a PE sheath and a PP core. In such fibers, the surface energy and water compatibility is provided by the PE sheath (typically treated with additives or hydrophillic finishes), and the PP core enhances the fiber's structural capability. Both components exhibit the requisite translucency behavior.

In some embodiments of the invention, the primary wick layer/portion and the indicator layer/portion of an assay wick sufficiency indicator may both be bonded fiber structures. In such embodiments, the primary wick layer/portion may be formed from fibers (e.g., polyolefin fibers) that exhibit the required translucency behavior. The indicator layer/portion may use the same fiber materials, but it may, however, may be formed from other fiber materials that provide the desired flow characteristics. In either case, the bonded fiber indicator layer/portion may be dyed or otherwise treated to be a contrasting color that would become visible only upon sufficient wetting of the primary wick layer/portion by the appropriate analyte fluid.

As an alternative to surface indicia or coloring, some embodiments may have an indicator layer/portion (e.g., a bonded fiber structure) that is configured to exhibit increased translucency upon wetting and that is loaded with a colored particulate or other contrasting material that is revealed upon wetting of the indicator layer/portion. In such embodiments, the increased translucency of both the primary wick layer and the indicator layer upon wetting by the analyte fluid allows the contrasting material to be viewed. Similar contrasting materials could be added to some or all of the primary wick layer, which, in certain embodiments, could eliminate the need for a separate indicator layer.

As noted above, the indicator layers of the invention may be formed from polymer fibers, and may, in particular, be porous, bonded fiber structures having similar or different materials and flow properties to/from the primary wick layer. The indicator layers of the invention may also be formed from other materials including, but not limited to, metal, foam (open or closed cell), films, molded plastic, composites, and particulates. These materials may have a contrasting color throughout their structure or on a single surface or they may be formed with contrasting topographical features.

It will be understood that the wick structures used in the invention can be tailored to provide desired fluid characteristics. For fiber structures, this can be accomplished by a combination of fiber material selection, fiber diameter, and porosity of the wick structure. It will further be understood that the thickness of the wick structure (or the depth of the indicator layer/material, depending on the embodiment) in the sufficiency indicator portions of the assay wicks of the invention will be dependent on the degree of translucency of the material when wetted by the analyte fluid. This, in turn, may be dependent on the density of the wick structure and the relative difference in refractive index between the wick material and the analyte fluid. Thus, it can be seen that the various wick material characteristics can be tailored so as to optimize fluid flow characteristics and translucency for a given indicator depth.

Any or all of these characteristics can be adjusted to assure that the indicator layer/portion becomes visible only when an amount of analyte fluid sufficient to assure a desired reaction with the reagents of the analyte test section is present. In some cases, it may be desirable to include particular indicia on the indicator layer/portion. The wick structure and indicator depth could then be tailored so that the indicia only become readable upon wetting by a sufficient amount of analyte fluid.

Any or all of the assay wicks of the invention may be housed in a standard assay device casing. Typically, such casings allow for selective exposure of the wick receiving surface and one or more windows for viewing a visual indication from the analyte reaction portion of the wick. For some wicks of the present invention, a window may also be provided to view the sufficiency indicator portion of the wick.

The operation of any of the assay wicks of the invention is straightforward. When an appropriate analyte fluid is introduced to the receiving surface of the wick, it is transported through the receiving portion of the wick toward the analyte test section. In embodiments where the sufficiency indicator is upstream of the analyte test section, the analyte fluid is passed through the wicking portion(s) of the sufficiency indicator to the analyte test section. In embodiments where the sufficiency indicator portion of the wick is downstream of the analyte test section, the analyte fluid is passed through the analyte test section and into the wicking portion(s) of the sufficiency indicator section. In either case, as the primary wicking layer/portion of the sufficiency indicator is wetted by the analyte fluid, it will become more light transmittent (i.e., more translucent). Prior to introduction of the analyte fluid, the primary wicking layer/portion is essentially white or colorless. If the amount of analyte fluid is sufficient to fully infuse the primary wicking layer/portion of the sufficiency indicator, the primary wicking layer/portion will become sufficiently translucent that the contrasting color or indicia of the indicator layer/portion can be observed.

The wicks of the invention have a wide applicability and may be used in conjunction with virtually any analyte fluid, including biological analyte fluids such as urine, plasma, serum, sweat, lachrymal fluid (tears), and saliva. Moreover, the wicks of the invention may be used in assay devices for detecting one or more analytes including, but not limited to, hormones such as human chorionic gonadotropin (hCG) frequently used as a marker for pregnancy, antigens, enzymes, antibodies to HIV, antibodies to HTLV, antibodies to *Helicobacter pylori*, antibodies to hepatitis, antibodies to measles, hepatitis antigens, antibodies to terponemes, antibodies to host or infections agents, cellular markers of pathology including, but not limited to, cardiolipin, lecithin, cholesterol, lipopolysaccaride and sialic acid, antibodies to mumps, antibodies to rubella, cotinine, cocaine, benzoylecgonine, benzodizazpines, tetrahydrocannabinol, nicotine, ethanol theophylline, phenytoin, acetaminophen, lithium, diazepam, nortriptyline, secobarbital, phenobarbital, theophylline, testosterone, estradiol, 17-hydroxyprogesterone, progesterone, thyroxine, thyroid stimulation hormone, follicle stimulating hormone, luteinizing hormone, transforming growth factor alpha, epidermal growth factor, insulin-like growth factor I and II, growth hormone release inhibiting factor, IGA and sex hormone binding globulin; and other analytes including glucose, cholesterol, caffeine, cholestrol, corticosteroid binding globulin, PSA, or DHEA binding glycoprotein.

Figure 10:
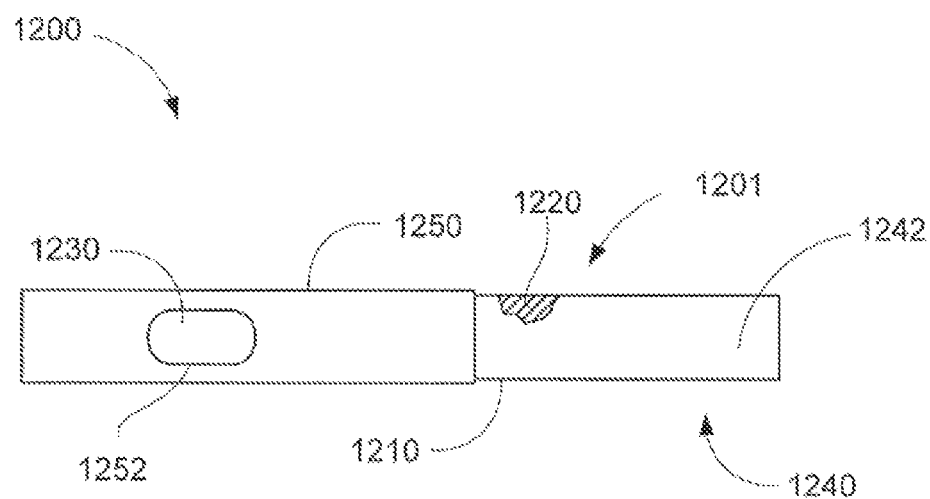
FIG. 10 is a top view of an assay device incorporating a sufficiency indicator wick according to an embodiment of the invention.
Figure 11:
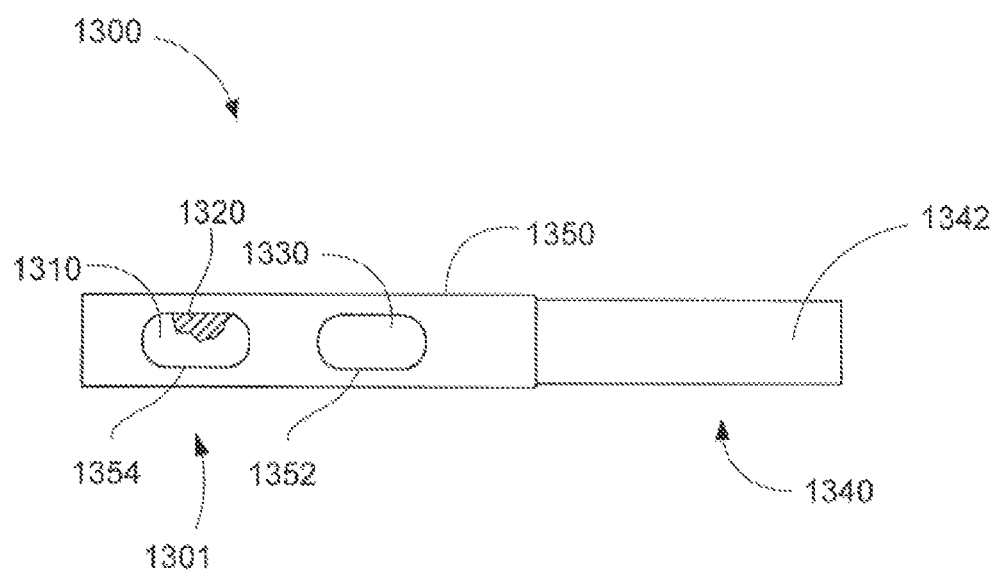
FIG. 11 is a top view of an assay device incorporating a sufficiency indicator wick according to an embodiment of the invention.

As has been discussed, the sufficiency indicator wicks of the invention may be used in a variety of assay devices. FIGS. 10 and 11 depict two exemplary assay devices that could make use of these wicks. In FIG. 10, an assay device 1200 has a housing 1250 in which is disposed an analyte test section 1230 that is viewable through a window 1252 in the housing 1250. The analyte test section 1230 is in fluid communication with a sufficiency indicator section 1201 comprising a primary wick portion 1210 and an indicator portion 1220, which may be configured according to any of the embodiments disclosed above. The primary wick portion is also in fluid communication with an analyte receiving section 1240 having a receiving surface 1242. Analyte fluid received by the receiving section 1240 is wicked by the primary wick portion to the analyte test section 1230 where it can be reacted with agents disposed there. The reaction may be viewed through the window 1252. The indicator section 1201 is configured so that the indicator portion 1220 is concealed by the primary wick portion 1210 unless or until the primary wick portion 1210 has been wetted by a sufficient amount of analyte fluid. When sufficiently suffused with analyte fluid, the contrasting characteristic of the indicator portion 1220 can be viewed through the primary wick portion 1210.

In the illustrated embodiment, some of the primary wick portion 1210 is disposed inside the housing 1250 and some is exposed outside the housing along with at least some of the indicator portion 1220 so that the indicator portion 1220 can be viewed when the primary wick portion is wetted. In an alternative embodiment, the entire indicator section 1201 may be disposed inside the housing 1250, but positioned to be viewed through the window 1252 or through an additional window (not shown). It will be understood that the receiving surface 1242 may be a surface of the primary wick portion 1210 or may be on a separate wick portion attached to or integrally formed with the primary wick portion 1210.

In FIG. 11, an assay device 1300 has a housing 1350 in which is disposed an analyte test section 1330 that is viewable through a window 1352 in the housing 1350. A sufficiency indicator section 1301 is disposed within the housing 1350 and in downstream fluid communication with the analyte test section 1330. The indicator section 1301 comprises a primary wick portion 1310 and an indicator portion 1320, which may be configured according to any of the embodiments disclosed above. The analyte test section 1330 is in fluid communication with an analyte receiving section 1340 having a receiving surface 1342. Analyte fluid received by the receiving section 1340 is wicked to the analyte test section 1330 where it can be reacted with agents disposed there. The reaction may be viewed through the window 1352. The analyte fluid is also passed to the indicator section 1301. The indicator section 1301 is configured so that the indicator portion 1320 is concealed by the primary wick portion 1310 unless or until the primary wick portion 1310 has been wetted by a sufficient amount of analyte fluid. When sufficiently suffused with analyte fluid, the contrasting characteristic of the indicator portion 1320 can be viewed through the primary wick portion 1310 and the window 1354.

It will be understood that many other assay device configurations are possible.

The preceding disclosure has focused on the use of the indicator wick sections of the invention as fluid sufficiency indicators. The wetted translucency behavior of the wick materials also allows embodiments of the invention to be used as indicators of a dry condition. For example, the indicator wick sections of the invention could be used as end-of-life indicators for air freshener devices such as those disclosed in U.S. application Ser. No. 12/099,942, filed Apr. 9, 2008, the complete disclosure of which is incorporated herein by reference in its entirety. In such an application, the indicator section would be incorporated into the air freshener wick with the characteristics of the primary wick portion being tailored to the air freshener fluid (the "analyte fluid"). Thus, the wicking material of the primary wick portion would be substantially transparent or translucent as long as the indictor section remained immersed in the air freshener fluid. Once that fluid runs out, however, the primary wick portion begins to dry out. As it does, it will become less and less light transmittent (i.e., more opaque) until, the indicator portion/layer is obscured. This effect can be used, for example, to make the wick appear the color of the indicator portion until the fragrance fluid is gone, at which time the wick turns colorless or white.

While the foregoing illustrates and describes exemplary embodiments of this invention, it is to be understood that the invention is not limited to the construction disclosed herein. The invention can be embodied in other specific forms without departing from the spirit or essential attributes.

What is claimed is:

1. A wick for use in determining sufficiency of an amount of analyte fluid provided to an analyte test section of an assay device, the wick comprising:
   a primary wick portion attached or attachable to the analyte test section so as to be in fluid communication therewith, the primary wick portion having a receiving surface adapted for receiving the analyte fluid into a first area of the primary wick portion and being configured to draw the analyte fluid from the first area to a second area of the primary wick portion; and
   an indicator portion having a contrasting visual characteristic, the indicator portion being disposed so that some or all of the indicator portion is covered by at least a portion of the primary wick portion,
   wherein the indicator portion is entirely non-wicking
   wherein the at least a portion of the primary wick portion comprises a first wicking material that becomes more light transmissive when the first wicking material is wetted by the analyte fluid,
   wherein the contrasting visual characteristic is viewable through the at least a portion of the primary wick portion only when the at least a portion of the primary wick portion is suffused by a predetermined amount of the analyte fluid, and
   wherein all of the indicator portion is located upstream or downstream of the analyte test section.

2. The wick according to claim 1 wherein the first wicking material comprises a plurality of fibers bonded to one another at spaced apart contact points, the fibers collectively defining tortuous fluid flow paths through the first wicking material.

3. The wick according to claim 2 wherein the plurality of fibers comprises fibers having at least one component comprising a polyolefin material.

4. The wick according to claim 2 wherein the plurality of fibers comprises fibers having at least one component comprising one of the set consisting of polypropylene and polyethylene.

5. The wick according to claim 2 wherein the plurality of fibers comprises sheath-core bicomponent fibers having a polyethylene sheath and a polypropylene core.

6. The wick according to claim 2 wherein the plurality of fibers comprises fibers having at least one component comprising a polyester material.

7. The wick according to claim 2 wherein the plurality of fibers comprises fibers having at least one component comprising a polyamide material.

8. The wick according to claim 1 wherein the contrasting visual characteristic is formed on a surface of the indicator portion and comprises at least one of the set consisting of a contrasting color, a pattern, and a graphical indicium.

9. The wick according to claim 1 wherein at least a portion of the indicator portion is a color that contrasts with a primary wick portion color.

10. The wick according to claim 1 wherein the at least a portion of the primary wicking portion has an upper surface and a lower surface and the indicator portion is positioned so that the indicator surface is in contact with the lower surface of the at least a portion of the primary wicking portion.

11. The wick according to claim 1 wherein the indicator portion is disposed within the primary wicking portion.

12. The wick according to claim 1 wherein the primary wicking portion is an annular cylinder.

13. The wick according to claim 12 wherein the indicator portion is a cylinder positioned coaxially within the primary wicking portion.

14. The wick according to claim 12 wherein the indicator portion is an annular cylinder positioned coaxially within the primary wicking portion.

15. The wick according to claim 1 wherein the receiving surface is configured to receive the analyte fluid from an external source and the primary wick portion is configured to draw the analyte fluid from the receiving surface to the analyte test section.

16. The wick according to claim 1 wherein the receiving surface is configured to receive the analyte fluid from the analyte test section.

17. The wick according to claim 1 wherein the analyte fluid is one of the set consisting of urine, blood, serum and saliva.

18. An assay device for use in processing an analyte fluid, the assay device comprising:
 a housing comprising at least a first window;
 an analyte test section disposed within the housing so that at least a portion of the analyte test section can be viewed through the first window;
 a primary wick portion being at least partially disposed within the housing in fluid communication with the analyte test section, the primary wick portion having a receiving surface adapted for receiving the analyte fluid into a first area of the primary wick portion and being configured to draw the analyte fluid from the first area to a second area of the primary wick portion; and
 an indicator portion having an indicator surface having a contrasting visual characteristic, the indicator portion being disposed so that the indicator surface is covered by at least a portion of the primary wick portion,
 wherein the indicator portion is entirely non-wicking
 wherein the at least a portion of the primary wick portion comprises a first wicking material that becomes more light transmissive when the first wicking material is immersed in the analyte fluid,
 wherein the contrasting visual characteristic is viewable through the at least a portion of the primary wick portion only when the at least a portion of the primary wick portion is suffused by the analyte fluid, and
 wherein all of the indicator portion is located upstream or downstream of the analyte test section.

19. The wick according to claim 18 wherein the contrasting visual characteristic is formed on a surface of the indicator portion and comprises at least one of the set consisting of a contrasting color, a pattern, and a graphical indicium.

20. The wick according to claim 18 wherein at least a portion of the indicator portion is a color that contrasts with a primary wick portion color.

21. The wick according to claim 18 wherein the housing further comprises a second window, the indicator portion is disposed within the housing, the at least a portion of the primary wick portion is visible through the second window, and the indicator portion is visible through the second window when the at least a portion of the primary wick portion is suffused by the analyte fluid.

* * * * *